(12) United States Patent
Hermsmeyer

(10) Patent No.: US 6,511,969 B1
(45) Date of Patent: Jan. 28, 2003

(54) METHOD FOR REDUCING CORONARY ARTERY REACTIVITY

(75) Inventor: R. Kent Hermsmeyer, Portland, OR (US)

(73) Assignee: Dimera, LLC, Portland, OR (US)

( * ) Notice: Subject to any disclaimer, the term of this patent is extended or adjusted under 35 U.S.C. 154(b) by 0 days.

(21) Appl. No.: 09/548,476

(22) Filed: Apr. 13, 2000

Related U.S. Application Data

(63) Continuation of application No. 09/024,972, filed on Feb. 6, 1998, now Pat. No. 6,056,973, which is a continuation-in-part of application No. 08/806,358, filed on Feb. 26, 1997, now abandoned.

(51) Int. Cl.[7] .......................... A61K 31/56; A01N 45/00
(52) U.S. Cl. .................. 514/177; 514/170; 514/182
(58) Field of Search .................... 424/449; 514/171, 514/177, 843, 861, 863, 899, 970, 170, 182

(56) References Cited

U.S. PATENT DOCUMENTS

| | | | |
|---|---|---|---|
| 4,900,734 A | 2/1990 | Maxson et al. | |
| 5,422,119 A | 6/1995 | Casper | |
| 5,859,001 A | 1/1999 | Simpkins et al. | |
| 5,985,861 A | * 11/1999 | Levine et al. | 514/170 |
| 6,054,447 A | * 4/2000 | Levine et al. | 514/177 |

FOREIGN PATENT DOCUMENTS

| | | |
|---|---|---|
| EP | 0 279 977 A2 | 8/1988 |
| WO | WO 95/07699 | 3/1995 |
| WO | WO 96/09826 | 4/1996 |

OTHER PUBLICATIONS

Ford, SP, et al., "Role of Estradiol–17β and Progesterone in Regulating Constriction of Ovine Uterine Arteries", Biology of Reproduction, 17:480–483 (1977).

White, MM, et al., "Estrogen, Progesterone, and Vascular Reactivity; Potential Cellular Mechanisms", Endocrine Review, 16(6):739–751 (1995).

Rylance, PB, et al., "Natural Progesterone and antihypertensive action", British Medical Journal, 290:13–14 (1985).

Miyagawa K., et al., "Medroxyprogesterone interferes with ovarian steroid protection against coronary vasospasm", Nature Medicine, 3(3):324–327 (1997).

Miyagawa K., et al., "$Ca^{+2}$ release mechanism of primate drug–induced coronary vasospasm", American Journal of Physiology, 272:H2645–H2654 (1997).

Jiang, C, et al., "Progesterone Induces endothelium–independent relaxation of rabbit coronary artery in vitro" European Journal of Pharmacology, 211:163–167 (1992).

Karmazyn, M. et al., "The Mechanism of Coronary Artery Spasm: Roles of Oxygen, Prostaglandins, Sex Hormones and Smoking", Medical Hypotheses, 5:447–452 (1979).

The Writing Group for the Pepi Trial, "Effects of Estrogen or Estrogen/Progestin Regimens on Heart Disease Risk Factors in Postmenopausal Women", Journal of American Medical Association, 273(3):199–208 (1995).

* cited by examiner

*Primary Examiner*—Russell Travers
*Assistant Examiner*—Lauren Q. Wells
(74) *Attorney, Agent, or Firm*—Howard Eisenberg, Esq.

(57) ABSTRACT

A method for reducing coronary artery reactivity. A predetermined amount of natural progesterone is provided by a convenient and pleasant delivery system to the blood stream, sufficient to reduce the likelihood of coronary vasospasm and myocardial ischemia. The progesterone may be provided either by topical application to the epidermis of a cream in which the progesterone is dissolved or by patch technology, so as to provide continuous delivery and thereby maintain the level of progesterone in the blood stream at least about 1 nanogram per milliliter.

6 Claims, 4 Drawing Sheets

METHOD FOR REDUCING CORONARY ARTERY REACTIVITY

RELATED APPLICATION

This application is a continuation of application Ser. No. 09/024,972, filed Feb. 6, 1998, which has issued as U.S. Pat. No. 6,056,973 and which is a continuation-in-part of abandoned U.S. application Ser. No. 08/806,358, filed Feb. 26, 1997 and entitled "Method for Reducing Coronary Artery Reactivity", the entire disclosure of which applications are incorporated herein by reference.

FIELD OF THE INVENTION

The invention relates to the use of progesterone to reduce coronary artery reactivity, as well as kits relating thereto. The invention also involves screening methods and animal models for testing the ability of a compound to reduce coronary artery reactivity.

BACKGROUND OF THE INVENTION

Cardiovascular disease, including coronary heart disease, stroke and other vascular diseases, is the leading cause of death of men and women in economically-developed countries. The most common and lethal form of cardiovascular disease is ischemic heart disease. It has generally been regarded that ischemic heart disease is caused, primarily, by atherosclerosis of the coronary arteries. This is a condition where plaques form in the inner lining of the arteries, causing narrowing of the channel and thereby impairing blood flow to the heart.

An increased risk for ischemic heart disease is observed in women after menopause or ovariectomy and presents a major medical challenge. It is the leading cause of death in post-menopausal women, which implicates the importance of the loss of ovarian steroid hormones.

Since it is understood that the formation of plaques is reduced, or even reversed by a high ratio of high density lipoproteins (HDL) to low density lipoproteins (LDL), it has been a strategy to inhibit ischemic heart disease by attempting to increase this ratio in the blood stream. Estrogen, an ovarian steroid hormone, has been observed to increase the HDL/LDL ratio, and studies so far suggest that estrogen replacement therapy for post-menopausal women decreases the incidence of coronary artery disease, myocardial infarction and related cardiovascular events by up to 50%.

The mechanism of estrogen's cardioprotective effects is not completely established, although a favorable impact on the circulating lipid and lipoprotein profiles is postulated as central to estrogen's cardioprotective effects. This explanation, however, is acknowledged to account for only a minority of estrogen's potential cardioprotective effects.

One important issue is the danger of using unopposed estrogen, which is believed to increase the risk of developing endometrial bleeding, endometrial cancer, or breast cancer. Progestins, including specially synthetic progestins, have been found to oppose these undesirable effects of estrogen replacement. In particular, progestins have been shown to stop bleeding and reduce the risk of cancer in women receiving estrogen as hormone replacement therapy. But even this use of progestins is controversial, in that at least one study indicated that the combination of estrogen and progestin appeared to have a greater stimulatory effect on cell division than estrogen alone, suggesting that the risk of breast cancer is increased when estrogen is combined with progesterone. (See U.S. Pat. No. 5,543,150). Likewise, it has been reported that progesterone and synthetic analogs such as medroxyprogesterone acetate (MPA) cause modest reductions in serum HDL levels.

A variety of synthetics progestins were developed because the natural hormone progesterone (the chemically explicit and unique name of a defined steroid molecule) is quickly metabolized in the liver. Oral dosages of progesterone are typically very high and involve flooding the liver with progesterone, whereby a fraction of the dose escapes metabolism and enters the blood stream. Not only is an extraordinary high dose necessary (200 milligrams per day or more), there also is evidence that hepatic progesterone metabolites have adverse side effects.

Various attempts have been made at other delivery forms for progesterone, although such attempts have been largely unsuccessful because of undesirable fluctuation in serum levels, inconvenience of administration, and the like. Typically, when administered, progesterone is given in amounts to produce serum levels of at least 6 nanograms/ml, and typically to produce in the range of 10 nanograms/ml to 12 nanograms/ml.

It was indicated 20 years ago that progesterone can inhibit hypoxia-induced vasospasm, which resulted in the proposal that prostaglandin inhibitors such as indomethacin or chloroquine, nitrites and prostacyclins could be used to prevent cardiac damage from such vasospasm. It was not stated what levels of progesterone were administered to inhibit such hypoxia-induced vasospasm and progesterone itself was not suggested as a therapeutic to inhibit such vasospasm, perhaps because of the controversy surrounding the use of progesterone as a therapeutic agent. M. Karmazyn, et al., *The Mechanism of Coronary Artery Spasm:Roles of Oxygen, Prostaglandins, Sex Hormones in Smoking*, Medical Hypothesis 5:447–452 (1979).

A vasospasm is an abnormally strong and persistent contraction of the muscles of the coronary arteries which leads to trasmural myocardial ischemia and can result in sudden cardiac death. The role of coronary vasospasm in cardiovascular disease is still controversial, and approaches to treatments for cardiovascular disease have not focused upon methods for reducing coronary vasospasm. Instead, it is generally believed that coronary vasospasm is caused by local injury to vessels, such as result from atherosclerosis and other structural injury, and that long-term treatment of cardiovascular disease requires prevention of atherosclerotic plaques, not treatments to prevent vasospasm.

U.S. Pat. No. 5,543,150 relates to a vaginal administration of progesterone to prevent endometrial cancer. The '150 patent teaches that the local concentration of progesterone in the endometrial tissue is on the order of 7 nanograms/ml, which is sufficient to produce secretory transformation of the endometrium. The '150 patent states that the systemic concentration of progesterone in the blood stream, remote from the endometrium, is between 1 and 2 nanograms/ml. According to the '150 patent, the beneficial endometrial effects of progesterone are obtained at levels of 7 nanograms/ml, while the risk of breast cancer presented by progesterone therapy is remote because serum levels are only about 1 to 2 nanograms/ml, lower than those known to have any side-effects remote from the endometrium. It specifically is stated that the coronary vasodilating effect of estrogen is not reversed by such concentrations of progesterone, i.e., there was no indication of an adverse effect of progesterone.

SUMMARY OF THE INVENTION

It has been discovered, surprisingly, that very low levels of progesterone can inhibit coronary artery reactivity and, therefore, can be used to inhibit certain adverse cardiovascular events and disorders. Also surprisingly, progesterone's protective effect was in contrast to the effects seen with the synthetic progestin MPA, in that MPA increased coronary artery reactivity. It also has been discovered that coronary artery reactivity is independent of vascular injury and can be mimicked in an animal free of plaques and known vascular injury. It further was discovered, surprisingly, that progesterone not only mediates a genomic effect on coronary arteries, but also exerts a direct effect on coronary arteries.

According to one aspect of the invention, a method is provided for reducing in a human subject coronary artery reactivity to a vasoconstrictive substance. The method involves administering to the subject progesterone in an amount to achieve blood levels of progesterone of between 0.1 nanograms/ml and less than 4 nanograms/ml for at least 4 hours per day, and wherein said amount results in peak levels of progesterone of less than 6 nanograms/ml. In preferred embodiments, the blood levels of progesterone are between 1 nanogram/ml and less than 4 nanograms/ml, and most preferably between 1 nanogram/ml and 2 nanograms/ml. Even more preferably, the progesterone is administered in an amount to achieve such blood levels for at least 6 and preferably 12 or more hours per day.

The progesterone can be administered in a manner to achieve continuously such blood levels for periods of 1 day, 2 days, 3 days or more. It is contemplated that the treatment will be applied daily over a period of months without interruption. The most preferred dosage form is a topical preparation applied to the epidermis. Such a preparation avoids the first-pass through the liver, and the skin acts as a slow-release mechanism for providing the above-noted amounts of progesterone. Surprisingly, it has been determined that a single topical application, once each day, can result in the desired levels of progesterone for more than 4, 6, 12 and even up to 24 hours, without exceeding the peak levels (6 nanograms/ml). Another form of administration can be an implant containing sufficient amounts of progesterone to achieve the blood levels for at least 3 days, and preferably 30 days or more.

As mentioned above, the progesterone can inhibit coronary artery vasospasm in subjects that are free of observable plaques, who are apparently healthy and have no sign of vascular disease. Thus, the invention can be useful in subjects who are non-hypercholesterolemic. The subjects also may be nonarthritic and/or may be post-menopausal or ovariectomized.

According to another aspect of the invention, a method is provided for reducing in a female human subject, coronary artery reactivity to a vasoconstrictive substance. The method involves administering to the epidermis of the subject a topical preparation containing between 10 milligrams and 100 milligrams of progesterone. In some embodiments, the preparation contains between 20 and 50 milligrams of progesterone. The preparation can be administered only twice per day, preferably at 12 hours intervals. The preparation can even be administered only once per day and still achieve the desired therapeutic benefit.

According to another aspect of the invention, a kit is provided for dispensing a pharmaceutical. The kit includes a package which houses a container, a topical preparation containing progesterone in the container, a dispenser for dispensing a metered amount of the topical preparation, and instructions. The instructions are for dispensing an amount of the preparation which amount, when applied topically to the skin, achieves blood levels of progesterone of between 0.1 nanograms/ml and less than 4 nanograms/ml for at least 4 hours per day and, wherein said amount results in peak blood levels of progesterone of less than 6 nanograms/ml after said application. In one embodiment, the instructions are for dispensing between 10 and 100 milligrams of progesterone for daily application to the epidermis. In another embodiment, the instructions are for dispensing between 20 and 50 milligrams of progesterone for daily application to the epidermis. Preferably, the instructions are for dispensing an amount which achieves blood levels of between 1 nanogram/ml and 2 nanograms/ml for at least 6 hours per day. In one embodiment, the instructions are for daily application only twice per day and in another embodiment, the instructions are for daily application only once per day. In one preferred embodiment, the instructions are for treating or preventing a coronary condition.

In one embodiment, the instructions are attached to the container. In another embodiment, the container is a bottle and the dispenser is attached to the bottle. The dispenser can be a pump.

According to another aspect of the invention, another kit is provided. This kit includes a package containing a transdermal patch, and instructions for using the patch to treat a coronary condition. The patch includes a housing, a reservoir in the housing, a membrane attached to the housing, adjacent the reservoir, for placement against the epidermis of a human subject, and an adhesive attached to the housing for holding the membrane to the epidermis of the subject. Progesterone in a carrier is contained in the reservoir, and the patch is constructed and arranged to deliver an amount of progesterone to the epidermis of the subject to achieve blood levels of progesterone of between 0.1 nanograms/ml and less than 4 nanograms/ml for at least 4 hours per day. The amount results in peak blood levels of progesterone of less than 6 nanograms/ml for the period that the subject wears the patch. In a preferred embodiment, the progesterone is delivered in an amount to achieve blood levels of between 1 nanogram/ml and 2 nanograms/ml for at least 6 hours per day, and preferably for between 8 and 24 hours per day. In one important embodiment, the patch delivers between 10 milligrams and 100 milligrams of progesterone to the epidermis over the period, and in another embodiment the patch delivers between 20 milligrams and 50 milligrams of progesterone to the epidermis over the period when applied to the epidermis.

According to another aspect of the invention, a kit is provided for dispensing a pharmaceutical. The kit includes a package housing a plurality of individual dispensing packets, each packet containing a topical preparation of progesterone. The kit also includes instructions for dispensing from one or more of said plurality of packets an amount of the topical preparation which, when applied topically to the skin, achieves blood levels of progesterone of between 0.1 nanogram/ml and less than 4 nanograms/ml for at least 4 hours per day and wherein said amount results in peak blood levels of progesterone of less than 6 nanograms/ml after said application. In important embodiments, each packet contains between 10 milligrams and 100 milligrams of progesterone. In other important embodiments, each packet contains between 20 milligrams and 50 milligrams of progesterone. In certain embodiments, the instructions are for daily application only twice per day, or only once per day.

According to another aspect of the invention, a method is provided for screening the ability of a test compound to inhibit coronary vasospasm. The compound is administered to a coronary hyperreactive animal free of known coronary plaques and coronary injury. Conditions are applied to the animal which, in the absence of an inhibitory compound, would provoke a coronary vasospasm. The presence or absence of coronary vasospasm in the presence of the compound then is determined, the absence being indicative that the test compound is an inhibitor of coronary vasospasm. The preferred animal is a nonhuman primate, preferably a rhesus monkey. The conditions which are applied preferably are a combination of at least two vasoconstrictive agents, and most preferably a combination of serotonin and U46619.

According to still another aspect of the invention, a method is provided for provoking an arterial vasospasm in a non-human animal, preferably a mammal. A vasoconstrictive agent is applied by intracoronary injection (via a coronary catheter) to a coronary hyperreactive animal in amounts effective to produce a vasospasm. In important embodiments, the animal is a non-human primate, preferably a rhesus monkey, and the animal can be rendered coronary hyperreactive by ovariectomy. In important embodiments, the arterial vasospasm is a coronary artery vasospasm. Preferably, the vasoconstrictive agent is at least two different vasoconstrictive agents, most preferably serotonin and U46619. Most preferably, the animal is free of known coronary plaques and coronary injury.

In any of the foregoing therapeutic embodiments, the progesterone can be applied together with other hormone replacement therapy, particularly estrogen. The progesterone is believed not only to decrease coronary artery reactivity and counter the undesirable effects of estrogens that increase the risk of endometrial hyperplasia and cancer, but it also is believed to assist in retarding the development of osteoporosis and loss of cognitive function in post-menopausal or ovariectomized women.

These and other aspects of the invention are described in greater detail below.

DETAILED DESCRIPTION

Figure 1:
FIG. 1 is an angiogram depicting the absence of vasospasm in a coronary artery.

The invention relates to coronary artery reactivity and, in one aspect, involves the use of progesterone to prevent coronary artery vasospasm, thereby preventing cardiovascular disorders. A cardiovascular disorder as used herein means myocardial infarction, ischemic heart disease, heart failure, stroke, angina pectoris, and peripheral arterial vascular disease. Coronary reactivity, as used herein, is a measure of the amplitude and duration of a response of an artery to an applied stimulus. According to the present invention, methods are provided for reducing the reactivity of coronary arteries to a vasoconstrictive substance. These methods thus are adapted to prevent coronary vasospasm, a focal constriction believed to result from local vascular hyperreactivity to vasoconstrictive substances. Coronary artery reactivity can be measured indirectly or directly. Indirect measures include a cell's response, such as a vascular smooth muscle cell's response to serotonin (5 HT) and U46619 (a thromboxane $A_2$ mimetic) applied in vitro as described herein. Direct measures include in vivo animal vascular responses to conditions for inducing a coronary vasospasm, e.g. in vivo mechanical injury or in vivo treatment of a hyperreactive animal with a combination of serotonin and U46619, also described herein.

A vasospasm is an abnormally strong and persistent contraction of the muscles of the coronary arteries which leads to transmural myocardial ischemia and often results in sudden cardiac death. The vasospasm causes the coronary artery to assume a characteristic "hourglass" shape of prolonged constriction. The term "vasospasm" is often misused in the literature to refer to a vasoconstriction which, rather than being abnormal and life-threatening, is a normal, healthy contraction as a means of autoregulating blood flow. As used herein, a coronary vasospasm is defined as epicardial coronary arterial constriction to <25% of control diameter in focal areas with adjacent downstream dilation, with an hourglass pattern thus formed persisting for >5 minutes.

It is believed that the abnormal muscle contractions of the vasospasm are caused by hyperreactivity of the coronary arteries. It is further believed that emphasis on atherosclerosis, LDL and the effect of progestins thereon has masked and/or been confused with this coronary artery hyperreactivity and increased risk of coronary vasospasm which is believed to be a fundamental mechanism contributing to ischemic cardiac disease. It has been discovered, surprisingly, that natural progesterone, as opposed to synthetic progestins, has a direct effect on vascular smooth muscle cells and can reduce coronary artery hyperreactivity. This results in an inhibition of vasospasm. It is believed that the frequency of vasospasm is greater than has previously been thought, and that vasospasm is the cause of a significant number of cases of ischemic heart disease. Natural progesterone, therefore, can be an effective preventative treatment.

It also has been found, surprisingly, that natural progesterone may be employed at very low doses, such as only one nanogram/ml of blood, which are ¼ to ⅒ the amount of natural progesterone normally present in women during the menstrual cycle and which is below the levels of progesterone previously thought necessary to have a beneficial effect when given to post-menopausal or ovariectomized women.

Although the present invention has arisen out of comparative studies as natural progesterone and synthetic progesterones, particularly MPA, in female rhesus monkeys, it will be understood by a person of ordinary skill in the art, that the results of these studies are directly applicable to female human beings. This is because female rhesus monkeys have been established as an excellent animal model for the physiological effects of female sex hormones on women.

These experiments also provide a basis for progesterone as a prophylactic treatment for myocardial ischemia in men because dilation in response to intra coronary injections of physiological levels of progesterone also are found in males.

Thus, the invention is useful in men and women. The invention is particularly useful in women who have abnormally low levels of progesterone, due to natural circumstances, surgery or disease. Typically such women are post-menopausal or ovariectomized. Such women can be otherwise healthy. In particular, such women can be non-arthritic and non-hypercholesterolemic. In this regard, the invention has provided the surprising finding that coronary hyperreactivity can be independent of atherosclerosis and progesterone can have its effect directly on an artery, not via lipid pathways.

Animal studies using female rhesus monkeys, described below, have revealed that coronary vasospasm occurs, in the absence of injury, plaques or other vascular pathology, due to local regions of vascular muscle hyperreactivity. In particular, vasospasm occurs in rhesus monkeys in the absence of atherosclerosis, which demonstrates that pure reactivity is sufficient to account for practically stopping vital coronary blood flow. Coronary vasospasm leads to transmural myocardial ischemia and often results in sudden cardiac death. Moreover, it has been found that such vascular muscle hyperreactivity can be revealed by the provocation, or challenge, with intracoronary injection of certain vasoconstricting agents. Thus, it has been found in these rhesus monkeys that are fed high fiber diets which prevent atherosclerosis, that life-threatening myocardial ischemia resulting from coronary vasospasm can be stimulated by drugs in the absence of atherosclerosis or other vascular pathology.

The invention is useful in subjects who are otherwise apparently healthy. Apparently healthy, as used herein, means individuals who have not previously had an acute adverse cardiovascular event such as a myocardial infarction (i.e. individuals who are not at an elevated risk of a second adverse cardiovascular disorder due to a primary cardiovascular event). Apparently healthy individuals also do not otherwise exhibit symptoms of disease. In other words, such individuals as examined by a medical professional, would be characterized as healthy and free of symptoms of disease.

The invention likewise is useful in "non-hypercholesterolemic subjects". Such subjects do not fit the current criteria established for a hypercholesterolemic subject. Hypercholesterolemic subjects are associated with increased incidence of a cardiovascular disorder. A hypercholesterolemic subject has an LDL level of greater than 190 mg/dl, or greater than 160 mg/dl and at least two risk factors selected from the group consisting of a family history of premature coronary heart disease, cigarette smoking (more than 10 per day), hypertension, low HDL (<35 mg/dl), diabetes mellitus, hyperinsulinemia, abnormal obesity, high lipoprotein (a) and personal history of cerebral vascular disease or occlusive peripheral vascular disease, or greater than 130 mg/dl if ischemic heart disease is present.

The invention thus is useful in connection with treating populations of patients never before treated with progesterone. Such patients can be free of symptoms calling for progesterone treatment. According to the art, progesterone has been described as useful for treating arthritic patients. The present invention is useful in the treatment of non-arthritic subjects. For the definition of this and other medical terms not specifically defined herein, see *Harrison's Principles of Experimental Medicine*, 13th Ed., McGraw-Hill, Inc., NY, N.Y.

The invention involves the administration of natural progesterone to subjects at the levels indicated above. The studies forming the basis of this application compared the effects of progesterone plus estrogen versus MPA plus estrogen on coronary reactivity. Surprisingly, MPA negated the protective effect of estrogen on coronary reactivity and, in fact, prolonged the contraction and increased the likelihood of vasospasm and ischemia. Natural progesterone, on the other hand, did not interfere with the protective effects and, in fact, independently acted most probably at both a genetic level and a direct level on vascular smooth muscle cells to reduce the reactivity of the coronary artery response amplitude and duration.

To achieve optimal prophylactic effects, progesterone is administered continuously to provide the desired blood levels. It has been discovered surprisingly, that progesterone applied topically can achieve the desired levels of progesterone in the blood stream for at least 4, 6, 12 and even 24 hours with only a single application. Prior art progesterone treatments are typically unsatisfactory because they are inconvenient, because they do not provide continuous blood progesterone levels, because they provide levels that are so high as to produce undesirable side effects, or a combination of the foregoing.

The preferred formulation is a topical preparation. As used herein, topical means applied externally to the surface of the skin. Specifically excluded are cavities such as the vaginal, rectal or oral cavity. Also excluded is the corneum. One existing product, currently sold under the trademark Pro Gest®, available from Transitions For Health, Inc. of Portland Oreg., USA, contains progesterone dissolved to a concentration of about 20 mg/ml. Because progesterone is insoluble in water, it should be dissolved in a non-polar oil. Vitamin E (Tocopherol) is used for this purpose in the formulation, and Aloe vera and other water-based substances are included as additives to achieve a pleasant skin cream.

The effectiveness of progesterone in such a cream as a delivery system is believed to be due to the combination of direct transdermal absorption of progesterone into the subject's bloodstream and the slow rate of transdermal absorption. As a consequence, progesterone in the cream formulation applied to the skin is absorbed and released over many hours, and is released directly into the blood stream so that it is not first metabolized into an inactive form, as would happen to natural progesterone absorbed by the digestive system.

Topical preparations, as known in the art, typically are non-solid, liquid, cream or ointment preparations. They may contain skin penetration enhancers. Skin penetration enhancers are agents that when co-applied with a drug to the skin enhance the ability of the drug to penetrate the skin and be delivered into the blood stream. Skin penetration agents are discussed in *Remington's Pharmaceutical Sciences*, Mack Publishing Co., 18th Edition, Easton, Pa., USA. (1990).

Patch technologies also can be used as a delivery system for progesterone. Transdermal patches typically include a housing, a reservoir in the housing and a membrane attached to the housing adjacent the reservoir for placement against the epidermis of the human subject. The patch has also included an adhesive attached to the housing for holding the membrane to the epidermis of the subject. Patches capable of delivering progesterone in the amounts according to the invention may be found in the following prior art patents: U.S. Pat. No. 3,731,683; U.S. Pat. No. 3,797,494; and U.S.

Pat. No. 4,336,243; U.S. Pat. No. 4,628,052; U.S. Pat. No. , 4,704,282; U.S. Pat. No. 4,788,062; U.S. Pat. No. 4,906,169; and U.S. Pat. No. 5,164,190, the disclosures of which are incorporated herein by reference.

A variety of administration routes, of course, are acceptable. The methods of the invention generally speaking, may be practiced using any mode of administration that is medically-acceptable, meaning any mode that produces the desired levels of progesterone without causing clinical unacceptable adverse effects. Such modes of administration include oral, rectal, vaginal, topical, sublingual, nasal, intradermal or other parenteral routes such as inhalation. Intravenous, intramuscular and oral routes are not particularly preferred or suitable for long-term therapy and prophylaxis.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a lipid carrier, a finely divided solid carrier, or both, and then, if necessary, shaping a product. As mentioned above, formulations suitable for various modes of administering can be found in Remington's Pharmaceutical Sciences.

Other delivery systems can include time-release, delayed release or sustained release delivery systems. Such systems can avoid repeated administrations of the active compound, increasing convenience to the subject and the physician. Many types of release delivery systems are available and known to those of ordinary skill in the art. They include polymer base systems such as poly(lactide-glycolate), copolyoxalates, polycaprolactones, polyester amides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di-and triglycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be desirable. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Figure 8:
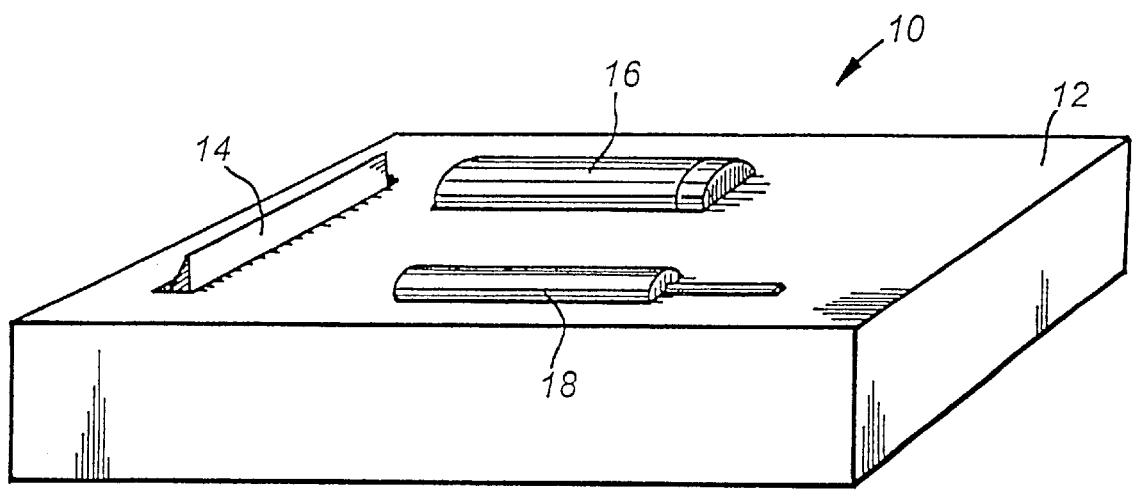
FIG. 8 is a kit according to the invention.

Referring to FIG. 8, the invention also includes various kits. Each of the kits includes instructions for dispensing an amount of progesterone to achieve the blood levels as described above. Each of the kits also contains in it a preparation of progesterone, either constructed and arranged to deliver the appropriate amounts of progesterone or with a dispensing means permitting dispensing of appropriate amounts of progesterone. Thus, the kit 10 includes a package 12 which houses instructions 14 as described above. The kit also includes a topical preparation of progesterone contained in a container 16 which, in this embodiment, is a bottle. A container may be any device for containing the progesterone, such as a bottle, vial, tube, packet and the like. This kit also includes a syringe 18 which may be used to withdraw from the container 16 the appropriate amount of the topical preparation of progesterone for use according to the invention.

In the kit depicted, the metering device is a syringe 18. The metering device, however, may be any such device known in the art for dispensing a metered amount of the preparation. For example, it may be a calibrated pump which is attached to the container 16 (i.e. a bottle with a pump dispenser) which is capable of delivering a metered amount of progesterone according to the invention. The dispensing device also can be simply a measuring cup or vial, or pressurized aerosol bottle. Any means for dispensing a predetermined amount of the progesterone is useful according to the invention.

The topical cream containing the progesterone also can be contained in individual packets, each packet containing an appropriate dose for topical application. The kit may include a plurality of such packets, such as 30, 60, 100 or more packets, each packet containing 2 ml of cream which in turn contains on the order of 25 mg of progesterone. The kits also can include transdermal patches, which have been described in detail above, as the means for both containing and the means for dispensing the metered amount of progesterone.

The invention also discloses methods for screening the ability of the test compound to inhibit coronary vasospasm. The method is described in general above, and in greater detail below. The method involves using a coronary hyperreactive animal. An animal may be rendered coronary hyperreactive by eliminating or suppressing the ovarian steroid hormones. This can be achieved by ovariectomizing an animal whereby otherwise suppressing ovarian steroid hormones chemically or even genetically.

The terms and expressions which have been employed in the foregoing specification are used therein as terms of description and not limitation, and there is no intention of the use of such terms and expressions of excluding equivalents of the features shown and described the portions thereof, it being recognized that the scope of the invention is defined and limited only by the claims.

EXAMPLES

EXAMPLE 1

Animals

We studied 10 adult rhesus monkeys (Macaca mulatta) 7 to 19 years old (average 13.4) in the main protocols described below and 5 additional monkeys in preliminary experiments. For the 10 main study animals, we used 1 male (14 years old) weighing 10.3 kg and 9 ovariectomized (ovx) female monkeys weighing 5.3 to 8.2 kg (average 6.2), none of which had been exposed to high cholesterol diets and which were later verified (see Results) to lack evidence of cardiovascular disease. Ovx rhesus monkeys were entered into the study no less than 3 months after ovariectomy.

Catheterization Studies

Angiography at the Dotter Institute, after overnight fasting, began with preanesthesia with ketamine (10 mg/kg body weight intramuscular), intubation with an endotracheal tube and a light surgical plane of anesthesia with isoflurane (induced at 1.5% to 3% maintained at 0.75% to 1.25%), vaporized with 33% nitrous oxide and 67% oxygen. Bilateral femoral intraarterial catheters allowed for coronary catheterization and continuous recording of systemic arterial blood pressure and heart rate, which were maintained close to the initial anesthetic value for each monkey. Intravenous heparin (1,000 U) was injected, and up to 120 ml of lactated Ringer's solution and 0 to 10 ml of dextran solution were used (as needed) to maintain diastolic blood pressure $\geq 60$ mm Hg. A heating pad assisted in maintenance of a body temperature decrease $\leq 2°$ C. of preanesthesia body temperature (monitored by rectal thermometer). An electrocardiogram (ECG) recorded on a Gould eight-channel recorder, cutaneous arterial oxygen saturation, respiratory rate and end-tidal $CO_2$ were also monitored.

Entire experiments were recorded on videotape (with episodic fluoroscopic imaging and continuous voice annotation) to permit computerized quantitative coronary angiography. Protocol 1 evolved from a series of pilot studies in five additional monkeys in which we tested different combinations and doses of the four vasoconstrictors serotonin, thromboxane $A_2$ (as U44619), endothelin-1 and angiotensin-II. Vasoconstrictor concentrations were incremented in log units because of the log-normal distribution of sensitivities in blood vessels. Because vasospasms were only observed in ovx monkeys in response to serotonin and U46619 in combination, we focused on this combination.

Placement of the 3F catheter (except as noted later) was adjusted to provide sufficient filling with radio-opaque contrast medium, limited reflux and isolation of a branch of the coronary arterial tree. Usually the left anterior descending coronary artery (LAD) was chosen, but the left circumflex (in two cases) or right coronary artery (in one case) was used instead, based on optimal placement and to avoid occlusion of blood flow. After adjustment of the camera angle to optimally image the coronary vascular tree, warm (35 to 38° C.) 1- to 2-ml boluses of Hexabrix (Mallinckrodt) radio-opaque contrast media were injected rapidly by hand to fill optimally. Fluoroscopic images were recorded on film using a Toshiba CAS-CP Angiorex system with fluoroscopic C-arm, developed immediately and evaluated for suitability of subsequent analysis. All procedures including a brief 0.2 ml injection of Hexabrix for optimal quantitative angiography were recorded on videotape for subsequent computer analysis.

Every injection of drugs was made by intra-coronary (IC) route, with a slow, constant flow of 1 ml over 30±1s. The time between drug injections was typically 7 to 10 min, and no less than 4 min, with pressures and heart rates allowed to return to $\leq 15\%$ change from baseline before the next injection. All concentrations given in the Methods section are syringe concentrations (uncorrected for dilution by coronary blood flow) to exactly describe the procedure. (The effective concentrations in the blood are presented in the Results section and in Table 3, as explained later).

Protocol I was the sequence of injections followed for the seven ovx monkeys. Step 1, IC injection of contrast media, established control coronary diameters; step 2 was slow IC injection of 1 ml of 100 nmol/liter of acetylcholine (ACh), a total of 0.018 µg, to validate endothelial function, as observed by vasodilation of large coronary arteries. Step 3 was IC injection of 1 ml of 1 µmol/liter (a total of 0.18 µg) ACh to show dilator capacity. The higher ACh dose is about 500 times less than the 100 µg used for provoking vasospasm in susceptible patients.

The fourth step in protocol was 1 ml of 100 µmol/liter serotonin (a total of 17.6 µg), a vasodilator dose that provided an additional test of endothelial dilator function. The fifth step was to inject 1 ml of 1 mmol/liter serotonin to directly vasoconstrict VMC. The sixth and seventh steps were injection of 1 ml of 100 nmol/liter U46619 (0.035 µg) and 1 ml of 1 µmol/liter U46619.

The eighth to tenth steps, which were 1 ml injections of 100 µmol/liter serotonin and 1 µmol/liter U46619 combined, were the critical steps. These concentrations of serotonin and U46619, injected in three repeated challenges, provoked drug-induced vasospasm. Sensitivity was determined by whether the vasospasm response occurred to the first, second or third stimulus, allowing at least a 7-min delay from one injection to the next. For three of these seven ovx monkeys, 1–2 nM endothelin-1 (alone and plus serotonin) and 1 µmol/liter angiotensin-II (alone and plus serotonin) steps were administered between steps 10 and 11 (as additional challenges), but these extra steps never produced vasospasm. Step 11, used only in the two ovx monkeys in which vasospasm was not found by this point, was the triple combination (in 1 ml) with 1 nmol/liter ET1, which also did not produce vasospasm. Step 12 was a $Ca^{2+}$ antagonist, either nitrendipine or mibefradil, as a vasodilator to relieve the vasospasm or cardiogenic shock that was the end point.

A separate mechanical injury, Protocol 2, was used in three additional monkeys (one male, two ovx). The injury step of protocol 2 was deliberate mechanical stretching of the LAD or left main coronary artery with a 5F catheter. (Except in these three monkeys with deliberate mechanical injury, the other seven [protocol 1] monkeys were studied with 3F catheters only to avoid mechanical injury, as verified by 1) lack of constriction at the catheter tip 2) no occlusion of coronary flow by the catheter, and 3) no evidence of injury on dissection and histopathologic examination as described later).

In Protocol 2, steps 1–5 were the same as in Protocol 1. The remaining steps were as follows:

6. IC injection of endothelin-1 (sequential doses to 10 nmol/liter);
7. IC injection of angiotensin II (sequential doses to 10 µmol/liter);
8. Injury by stretching the coronary artery with a 5F catheter;
9. IC injection of serotonin (sequential doses to 1 mmol/liter);
10. IC injection 15 min later with 1 or 10 µmol/liter nitrendipine or Ro 40-5967 (mibefradil);
11. IC injection of U46619 (sequential doses to 10 µmol/liter); and
12. IC injection 15 min later with 1 or 10 µmol/liter nitrendipine or Ro 40-5967.

Concentrations of Drugs in Coronary Blood

Effective autacoid concentration (as diluted by blood flow) at the vascular muscle cell (VMC) membrane is critical but elusive. We based the analysis in Table 1 on the following assumptions. All injections were 1 ml, infused by hand steadily over a 30-s interval. The concentrations in the syringe would have been diluted instantaneously by coronary blood flow. Based on size, the 3F (1.0-mm outer diameter) catheter (area 0.785 $mm^2$) would occlude coronary blood flow in the average 1.35-mm diameter coronary artery (area 1.43 $mm^2$) by 54% (under the preconstriction conditions). With coronary blood flow of 30 ml/min in this case, the concentration reaching a VMC would therefore be diluted about 15 times, or more with distance from the injection point.

However, the blood flow through individual epicardial arteries (LAD or left circumflex) would have represented only part of total coronary flow, offsetting the downstream dilution. We compromised on the factor of 15 times for the Table 1 concentrations, although we acknowledge that this is only an approximation.

Coronary Artery Diameter Measurement

Putative coronary vasospasm stimuli were judged primarily by actions on large coronary artery diameters, analyzed as diameter of the most proximal focus of vasospasm at end-diastole from video-taped images recorded at 30 frames/s. We used the image analysis program Image Pro to measure the diameters from single frames acquired with an Imagraph frame grabber in a Pentium computer. We used the 3F catheter tip radio-opaque marker ring (1.0 mm) for calibration and determined minimal and maximal diameters just distal to the constriction. All responses to interventions were also X-ray imaged immediately (15 to 30 s after injection) and at exactly 3 min (and 15 min if there was vasospasm) after injection. Inter-observer variability (coefficient of variation) was 7% on repeat measurements, as tested on selected samples.

Statistical Analysis

Results are expressed as mean value±SEM for all variables measured. Statistical significance was determined by analysis of variance with Bonferroni protected paired t tests. Values of $p \leq 0.05$ were accepted as significant.

ing (half-log units) concentrations to find the reduction of artery diameter by 50%. We used 10 times as the multiplier (where practical) to reach the maximal dose to be tried (Table 1). No vasoconstrictor alone caused coronary vasospasm, even though there were transient reductions to 20% of control diameter. The first injection in protocol 1 was a low dose of 6.7 nmol/liter ACh to test endothelial integrity, as judged by vasodilation, which was sufficient in sensitive arteries (three females, one male), whereas 67 nmol/liter ACh produced immediate vasodilation within 15 s in all monkeys.

Intra coronary injections of serotonin from 67 nmol/liter to 667 μmol/liter were vasoactive in all animals.

These serotonin-induced contractions appeared uniform along the length of the arteries, with no evidence of the characteristic vasospasm hourglass profile.

Intra coronary injection of the stable $TxA_2$ mimetic U46619 in concentrations from 6.7 to 2,000 nmol/liter caused constriction of arteries in all 10 monkeys, predominantly due to constriction of small arteries and markedly increased total coronary resistance as indicated by fluoroscopy (resistance to injection and slow clearance of the radio-opaque contrast media).

Although blood pressure and cardiac contractility decreased with repeat injections of high $TxA_2$ doses, there was no coronary vasospasm with $TxA_2$ alone.

TABLE 1

Sensitivity to Vasospasm Stimuli

| | $ED_{50}$ (−log mol/liter) | $EC_{50}$ (−log mol/liter) | Max Dose (−log mol/liter) | Spasms/N | Protocol |
|---|---|---|---|---|---|
| Single stimulus Serotonin* | 2.5 | 3.8 | 2 | 0/8 | 1** |
| U46619 | 5.5 | 6.8 | 5 | 0/8 | 1** |
| Endothelin 1 | 8.5 | 9.8 | 8 | 0/3 | 2 |
| Angiotensin II | 5.5 | 6.8 | 5 | 0/3 | 2 |
| Combined stimuli Endothelin 1 + serotonin*** | 9 | 10.3 | 8 | 0/3 | 2 |
| Angiotensin II + serotonin*** | 6 | 7.3 | 5 | 0/3 | 2 |
| Mechanical injury + serotonin*** | NA | NA | NA | 3/3 | 2 |
| U46619 + serotonin*** | 6 | 7.3 | 5 | 5/7 | 1 |

*1 mmol/liter.
**One of the protocol 2 animals also was tested with serotonin alone and U46619 alone, after the angiotensin II step, accounting for the total of eight in the first two rows. Vasospasms all consisted of reduction to $\leq 25\%$ of control diameter with downstream dilation (hourglass shape) that persisted for $\geq 15$ min.
***100 μmol/liter.
$EC_{50}$ = estimated actual coronary artery blood concentration in −log mol/liter based on a 15-fold dilution, (for details, see Methods);
$ED_{50}$ = dose in μmol/liter = dose in μmol/liter (as the concentration in the syringe, without allowing for any dilution due to coronary blood flow) of the named vasoconstrictor that caused a 50% reduction of diameter from control;
Max Dose = maximal dose tried (syringe concentration) in −log mol/liter for each vasoconstrictor;
N = number of animals in a protocol;
NA = not applicable;
Spasms = number of animals with vasospasm.

Results

Protocols that Failed to Induce Coronary Vasospasm

Single-drug challenges. Coronary catheterization laboratory studies of vasoconstriction in male or ovx rhesus monkeys were begun by individually testing serotonin, $TxA_2$ mimetic (U46619), ET1 or AII by injection in increas- Endothelial 1 =T1) Alone or With Serotonin Addition of 6.7 μmol/liter serotonin increased sensitivity by three times; the estimated ETI $EC_{50}$ of the responsive ovx monkeys was 200 pmol/liter without and 67 pmol/liter with serotonin (Table 3). The triple combination with 67 nmol/liter U46619, used in the two ovx monkeys that failed to show vasospasm by this point, produced cardiogenic shock but not vasospasm; diastolic blood pressure fell to ≦20 mm Hg, and the heart was severely hypokinetic as observed by fluoroscopy.

Angiotensin II (AII) Alone or with Serotonin

Angiotensin II in concentrations up to 200 nmol/liter did not cause vasospasm but did increase systemic blood pressure. Although the combination with serotonin increased heart rate, there was no coronary vasospasm (Table 3).

Protocols that Induced Coronary Vasospasm

Mechanical injury. As a basis for comparison, we used deliberate injury to the coronary arteries inflicted by stretching with a catheter with deliberately roughened tip, in one male and two ovx monkeys. The stretch maneuver would cause injury to both endothelium and media and induce local vasoconstriction. Intra coronary injection of 67 μmol/liter serotonin subsequent to injury caused coronary vasospasm at multiple sites. Before injury, arteries were open and well filled. The 5F catheter was then advanced to produce injury by a single stretch at the point marked by the radio-opaque tip, which produced transient focal narrowing to 20% of control, with recovery to >50% in 4 min. We injected 67 μmol/liter serotonin (IC) 12 min later as 1 ml over 30 s (as explained in Methods), causing vasospasm evident at three focal points made prominent by three distal dilations (FIG. 1B) forming the classical hourglass pattern that mimics human coronary vasospasm. Vasospasm was relieved with injection of 10 μmol/liter nitrendipine (no dilution allowed for in this low blood flow condition), as shown by return to nearly control dimensions (except at the injury region near the catheter tip). Subsequent injection of 67 nmol/liter U46619 caused another vasospasm with the same foci as that for serotonin. Even in the deliberate catheter injury experiment, the vasospasm induced was not simply a local response to direct mechanical injury because vasospasm occurred not only at the point of artery wall injury, but also at foci several millimeters distal to the injury. Such characteristic focal contractions appeared at least 10 to 25 mm beyond the furthest point ever reached by guide wires or catheters. Focal constriction and downstream dilation occurred that would be consistent with punctate release or sites of hyperreactivity or both, because there was no evidence of occlusive emboli.

The injury was imposed with a 5F catheter that stretched the left main coronary artery. Vasospasm was stimulated by subsequent IC serotonin or 1 nmol/liter U46619 but not by ≦10 nmol/liter ET1 or ≦10 μmol/liter AII. With 4F catheters, there was also injury due to stretching and flow occlusion in these 25–45-g hearts. Mechanical injury was also used in two ovx monkeys (protocol 2), with multiple vasospasms similar to the results in the male monkey shown. However, in the remaining seven ovx monkeys, only 3F catheters along with protocol 1 were used to avoid injury to study purely drug-induced coronary vasospasm.

Combined Serotonin and $TxA_2$

Figure 2:
FIG. 2 is an angiogram depicting vasospasm induced by the combination of serotonin and U46619.

With the combination of 6.7 μmol/liter serotonin and 67 nmol/liter U46619, we found coronary vasospasm in five of seven ovx monkeys, even though vasospasm could not be found in response to 6.7 or 200 μmol/liter serotonin alone or 6.7 to 2,000 nmol/liter U46619 alone in the same seven animals Crable 1). None of the seven monkeys responded to the first serotonin and U46619 combination injection; two responded to the second injection; and 3 responded to the third injection with vasospasm. The two that did not show vasospasm nevertheless showed severe vasoconstriction. Sample angiograms showing vasospasm induced by the combination of serotonin and U46619 are displayed in FIGS. 1 and 2. The control condition (FIG. 1) shows a normally patent left main coronary artery filled with radio-opaque contrast media Constriction 15 s after the second injection of serotonin and U46619 is shown in FIG. 2B and after 3 min in FIG. 2C. All vasospasms observed in protocol 1 occurred >5 mm beyond the most distal point ever reached by either catheter or guide wire.

The onset of constriction to the serotonin and U46619 combination injection began immediately on arrival and was evident on the first film (1 5 s after the injection). The contraction progressed over the next 2 min, reaching a peak between 2 and 4 min from the end of injection. The number of vasospasm regions in a major artery averaged three (range one to six). When there was more than one vasospasm in an artery, the second and subsequent vasospasms occurred 5 to 25 mm distal to the first focal vasospasm. The hourglass pattern in FIG. 2 is similar to that in the mechanical injury plus serotonin vasospasm.

Life-threatening reductions in blood pressure and cardiac contractility resulted from such severe coronary ischemia. Diastolic blood pressure fell to <20 mm Hg in several monkeys, correlated with more than fivefold decreases in dP/dt values (cardiac contractility) and faint ventricular contractions observed fluoroscopically. Systolic blood pressure correspondingly fell to <40 mm Hg, and in several cases heart rate fell to <60 beats/min. Minimal diameter was severely reduced, in some loci to <0.1 mm (<8%), and downstream dilation was more than five times the diameter at the vasospasm focus. All variables except maximal diameter were significantly different from control values, as indicated by daggers in Table 2.

TABLE 2

Hemodynamic Variable Changes at Control, Serotonin and U46619 Combination and Recovery Steps in Drug-Induced Vasospasm Protocol in Seven Ovariectomized rhesus Monkeys*

|  | Control (mean ± SEM) | S + U (mean ± SEM) | Recovery (mean ± SEM) |
|---|---|---|---|
| Systolic BP (mm Hg) | 122 ± 7 | 83 ± 14** | 114 ± 10 |
| Diastolic BP (mm Hg) | 84 ± 6 | 43 ± 15** | 76 ± 11 |
| dP/dt max | 1,653 ± 437 | 305 ± 136** | 1,285 ± 548 |
| Heart rate (beats/min) | 107 ± 5 | 74 ± 18** | 126 ± 22 |
| Min diameter (mm) | 1.33 ± 0.45 | 0.22 ± 0.11** | 1.08 ± 0.76 |
| Max diameter (mm) | 1.35 ± 0.44 | 1.12 ± 0.68 | 1.21 ± 0.77 |

*All seven monkeys without mechanical injury are included in these data, whether showing vasospasm (5 monkeys) or not (2 monkeys). The three monkeys that received mechanical injury are excluded from the table.
**The monkey that did not recover (FIG. 2) is not included in these data.
**All serotonin and U46619 combination data except maximal diameter are significantly different from control and recovery data by Bonferroni protected t tests (p < 0.05).
BP = blood pressure;
diameter = point of greatest vasoconstriction (Min) and downstream dilation (Max) (in mm) before, during the peak of the serotonin and U46619 combination vasospasm and after recovery;
dP/dt max = maximal rate of increase of left ventricular blood pressure measured from the intraarterial blood pressure catheter in mm Hg/s.

Relief of Coronary Vasospasm

To allow monkeys to recover and prevent death due to cardiogenic shock, we followed combined serotonin and U46619 stimulation with an IC $Ca^{2+}$ antagonist, either nitrendipine or mibefradil, at the end of the 15 min vasospasm, except for that in FIG. 2. Intra coronary injection of 1 ml of 10 μmol/liter nitrendipine or 1 μmol/liter mibefradil (without allowing for dilution due to severely reduced blood flow) caused improved cardiac performance, beginning ~1 to 3 min after injection, with an increase in systolic and diastolic blood pressure and improved cardiac contractility (increased dP/dt). In monkeys with severe vasoconstriction and low heart rates (<90 beats/mm), $Ca^{2+}$ antagonists effected increases to 90 to 200 beats/min due to reversal of atrioventricular conduction blocks (evident in the recovery of heart rate shown in Table 2). Hemodynamic variables returned to levels not significantly different from control with the help of $Ca^{2+}$ antagonists, although there was a trend toward increased heart rate.

Nitrendipine (1 to 10 /mol/liter not allowing for dilution) injected IC was effective in eliminating the vasospasm, even in animals that had diastolic blood pressures as low as 20 mm Hg. Mibefradil (Ro 40-5967) IC injections at 0.1 to 10 $\mu$mol/liter (without allowing for any dilution by blood flow) were also immediately effective in relieving vasospasm and returning blood pressures from diastolic levels as low as 10 to 20 mm Hg back to normal ranges (minimums of 100/60 mm Hg for systolic/diastolic levels.

In all monkeys, $Ca^{2+}$ antagonists relieved vasospasm, allowing recovery of blood pressures, heart rate and contractility toward normal.

Pathologic Examinations

Gross structural abnormalities were not seen in any of the hearts. There was also no visible evidence of acute injury or pre-existing lesions in coronary arteries or the myocardium at or near the spasm foci.

Discussion

These results show that even in the absence of injury or plaques, stimulation by the combination of serotonin and a mimetic of $TxA_2$ evokes coronary vasospasm in ovx rhesus monkeys. The radiologic appearance and pharmacologic responses closely mimic characteristics of human coronary vasospasm found in diagnostic provocative testing with single injections of ergonovine, histamine or high dose ACh (12, 14, 16, 19, 29–32). The lack of epicardial vasospasm in response to single agonists is remarkable and probably accounts for the difficulty in provoking vasospasm in animals. The requirement for a combination of synergistic stimuli would suggest that the vasospasm phenomenon is complex.

EXAMPLE 2

Methods

Twelve rhesus monkeys (*Macaca mulatta*), aged 8 to 16 years and with weights of 5–7 kg, were ovariectomized at least 3 months prior to beginning of the study and selected randomly for one of two treatments. After documenting the lack of cardiovascular disease or previous exposure to atherogenic diet and after a normal physical examination (including blood chemistry), monkeys received subdermal sylastic implants containing 200 mg of $E_2$. Two weeks later, sylastic implants containing either 400 mg of P or 400 mg of MPA were additionally implanted. All steroids were purchased from Steraloids (Wilton, N.H.). Both estrogen and progestin implants, providing sustained release steroids, remained in place through the catheterization study 6 weeks after beginning the study. Venous blood sample (5 ml) were collected just prior to beginning the study at weekly intervals for measurements of serum levels of $E_2$, P, and MPA. Target levels of 80–160 pg/ml for $E_2$, 4000–8000 pg/ml for P, and 400–800 pg/ml for MPA were based on levels that are effective by reproductive system indices in women[12] and monkeys[18]. Levels were measured in blood serum at catheterization by specific radio-immunoassays.

Angiography was carried out under isoflurane (0.75–1.25%) general anesthesia with 70% $O_2$ and 30% $N_2O$, and body temperature supported with a heating pad. After ketamine sedation (10 mg/kg) and endotracheal tube placement, both femoral arteries were cannulated for simultaneous measurement of systemic blood pressure and coronary catheterization. Intravenous anticoagulation with 1000 units of heparin and fluid replacement with 75–150 ml of lactated Ringer's solution, and if needed 10–50 ml of dextran, to reach a minimum control diastolic blood pressure of 60 mm Hg.

Coronary arteries (left anterior descending or left circumflex) of the monkeys were catheterized and agents injected as described above in Example 1.

Statistical analysis was carried out by Student's t-test (non-paired) or Chi-square, with the $p<0.05$ level accepted as significant.

Table 3 shows the major finding of this study, which is that P in combination with $E_2$ protected against vasospasm while MPA did not. Every monkey (6 of 6) that had been exposed to MPA for 4 weeks with $E_2$ was sensitive to the S+U combination, and showed vasospasm before the protocol was complete. $E_2$+MPA treated monkeys (MPA group) responded to 1–5 S+U challenges (mean=2.7±0.7) with vasospasm. In contrast, the $E_2$+P treated monkeys (P group) never showed coronary vasospasm (0 of 6), even after 6 or more S+U doses, the last of which produced cardiogenic shock.

TABLE 3

Drug-induced coronary vasospasm incidence and steroid levels

| Parameter | P | MPA |
| --- | --- | --- |
| Vasospasms | ⁰⁄₆ | ⁶⁄₆* |
| $E_2$ (pg/ml) | 104 ± 10 | 99 ± 9 |
| P (pg/ml) | 6670 ± 676 | <100* |
| MPA (pg/ml) | <100 | 1737 ± 1129* |

All monkeys were treated with estradiol 17β via sylastic implants for the entire treatment period. P or MPA was added during the last 2 weeks as a second sylastic implant, to simulate the luteal phase (P) or hormone replacement therapy (MPA). All steroid implants were left in place, including during angiography. Steroid measurements were made by RIA[15] on serum samples taken just before angiography.
*Indicates significant differences between P and MPA at p 0.05 (N = 6 for each group).

Diameters ($\phi$) of the proximal LAD or left circumflex coronary arteries under control conditions averaged 1.14±0.21 for P and 1.15±0.10 mm for MPA groups. Dilator responses to low dose (0.8 $\mu$g) ACh were equal in P (1.20±0.25 mm) and MPA 1.21±0.19 mm) groups. However, vasoconstrictor stimulation with S+U resulted in minimum ($\phi$) significantly smaller in the MPA (0.15±0.04 mm) than in the P (0.37±0.02 mm) group, which represent 87% and 67% reductions from controls, respectively (Table 4).

TABLE 4

Coronary artery diameters ($\phi$), blood pressures. and heart rates

| Parameter | P | MPA |
| --- | --- | --- |
| Control ($\phi$) in mm | 1.14 ± 0.21 | 1.15 ± 0.10 |
| S + ($\phi$)_(minimum) | 0.37 ± 0.02 | 0.15 ± 0.04* |
| Control SBP in mm Hg | 101 ± 12 | 101 ± 13 |
| Control DBP in mm Hg | 60 ± 5 | 61 ± 5 |
| Control Heart rate in bpm | 130 ± 24 | 134 ± 26 |
| S + U stim SBP in mm Hg | 51 ± 18 | 45 ± 11 |

TABLE 4-continued

Coronary artery diameters (φ), blood pressures, and heart rates

| Parameter | P | MPA |
|---|---|---|
| S + U stim DBP in mm Hg | 30 ± 12 | 26 ± 8 |
| S + U stim Heart rate in bpm | 66 ± 34 | 69 ± 24 |

The S + U stimulated values represent the minimum (φ), blood pressure, and heart rate responses, measured at different times.
(φ) minimum times ranged from 3 to 5 min, and blood pressure and heart rate from 5–20 min after IC injection of S + U. Image analysis) Image Pro from Media Cybernetics, Silver Spring, MD) of single frames acquired via Imagraph (Chelmsford, MA) A–D conversion, from angiography recorded on videotape, allowed high resolution measurements of (φ).
*Indicates significant differences between P and MPA at $p < 0.05$ (N = 6 for each group).

Angiographic examples at the point of peak responses to intra coronary vasoconstrictor challenges in the P group were measured. Coronary arteries had normal dilator function, as indicated at the lower dose of serotonin or with ACh. Even with the potent S+U challenge repeated 6 or more times, there was no vasoconstriction and decreased contractile function, as shown by decreasing blood pressure 3–10 min after injection and ST segment changes in the EKG indicating myocardial ischemia.

Vasoconstrictions to S+U in the P group never showed the vasospasm hallmark pattern of focal constriction with downstream dilation.

In contrast, MPA monkeys were not protected against vasospasm. Although there was also apparently normal dilator function, as indicated by the low dose of ACh , IC injection of S+U resulted in segmental occlusion and vasospasm. This strong 92% constriction, including at least one hour-glass pattern, was sustained for 15 min, even longer than our criteria for vasospasm. After 15 min, IC mibefradil was injected to relieve the vasospasm and restore cardiac performance. Blood pressure, which reached a nadir of 38/20 mm Hg in this monkey returned to 124/84 mm Hg after IC mibefradil.

Serum levels of $E_2$ and P were within physiological ranges and MPA were in the low therapeutic range. $E_2$ levels were not significantly different between P and MPA groups, and both were near 100 pg/ml. The P levels were appropriate for the luteal phase range at about 7000 pg/ml, and MPA levels were in the in low therapeutic range for women on hormone replacement therapy, averaging about 600 pg/ml. The false indication of MPA observed in one of the P group is explained by cross-reaction of the antiserum with P that was more than 50 times higher. P levels falsely indicated in 3 MPA treated monkeys were only slightly above background.

EXAMPLE 3

VMC Preparation

Single VMCs from the left anterior descending, circumflex, and right coronary arteries of adult rhesus monkeys were isolated and studied both as freshly dispersed and as primary cultures. The short-term primary cultured cells (never passaged) maintain the characteristics of the source tissue for 2–3 weeks, including contraction, relaxation, receptors, and membrane electrical properties. VMCs were dissociated with collagenase and protease enzymes in a potassium glutamate solution (KG) that prevent loading with $Na^+$, $Ca^{2+}$, or $Cl^-$ and results in a high proportion of viable, contracting cells (Self, D. A., et al.,*J. Vasc. Res.* 31:359–366 (1994); Rusch, N. J., et al., *Physiology and Pathophysiology of the Heart*, 999–1010 (1995)). The cells prepared for culture were seeded at low density in cardiovascular culture solution for mammals, fifth generation (CVSM) on glass coverslips to facilitate selection of individual cells. VMC were used for experiments 7–14 days after attaching to coverslips.

Subcellular $Ca^2$ and PKC Localization

Freshly dispersed or primary cultured VMCs on glass coverslips were placed in a chamber of laminar flow design and observed with a Zeiss Plan Neofluar 25X/0.80 water immersion objective. Ionic solution for mammals version 2 (ISM2) was continuously pumped through the chamber (at 1 ml/min) to provide continuous equilabration and washout of drugs. After a 15 min equilibration period, VMC were loaded for 15 min at room temperature with 3 μM fluo 3 (Molecular Probes, Inc.) for sensing $Ca^{2-}$ and for 10 min with 30–100 nM hypericin (LC Laboratories) for reporting PKC. Individual VMC were stimulated by adding 20 μl of 10 μM serotonin plus 100 nM U46619 over the individual cell. After 15 sec under no-flow conditions, continuous flow of ISM2 was reinstated and a chamber volume of approximately 300 μl was maintained. Fluorescent images were taken at 1, 2, 5, 10, 15, 20 and 30 min after stimulation for $Ca^{2+}$ and at 3, 4, 9, 16, 21 and 31 min for PKC to evaluate subcellular distribution of these signals, and to determine VMC contraction.

Drugs and Solutions ISM2 contains (in mM): 100 NaCl, 4 $NaHCO_3$, 0.5 $NaH_2PO_4$, 4.7 KCl, 1.8 $CaCl_2$, 0.41 $MgCl_2$, 0.41 $MgSO_2$, 50 HEPES (pH 7.37), and 5.5 dextrose, KG solution consists of (in mM); 140 K-glutamate, 16 $NaHCO_3$, 0.5 $NaH_2PO_4$, 30 HEPES, and 16.5 dextrose at pH 7.3. CVSM consists of: 4.0 mM L-glutamine, 10 μg/ml ciprofloxacin (Miles Pentex/Bayer Corporation), 50 mM HEPES (pH 7.3), and 16 mM $NaHCO_3$ dissolved in 85% MEM-Earle's salts and 15% horse serum. Phenol red, known to have estrogenic activity, was omitted from all solutions.

As discussed above, the monkeys were implanted with subdermal sylastic tubing containing estrogen (E) progesterone (P) or MPA. The first step in each of the three groups was to implant sylastic tubing containing E. Two weeks later, either P or MPA were additionally implanted and maintained for another 4 weeks (6 weeks total). In the withdrawal (W) group, the E tube was withdrawn, and no tubes were implanted for the last 4 weeks.

Averaged $Ca^{2+}$ Signals.

Figure 3:
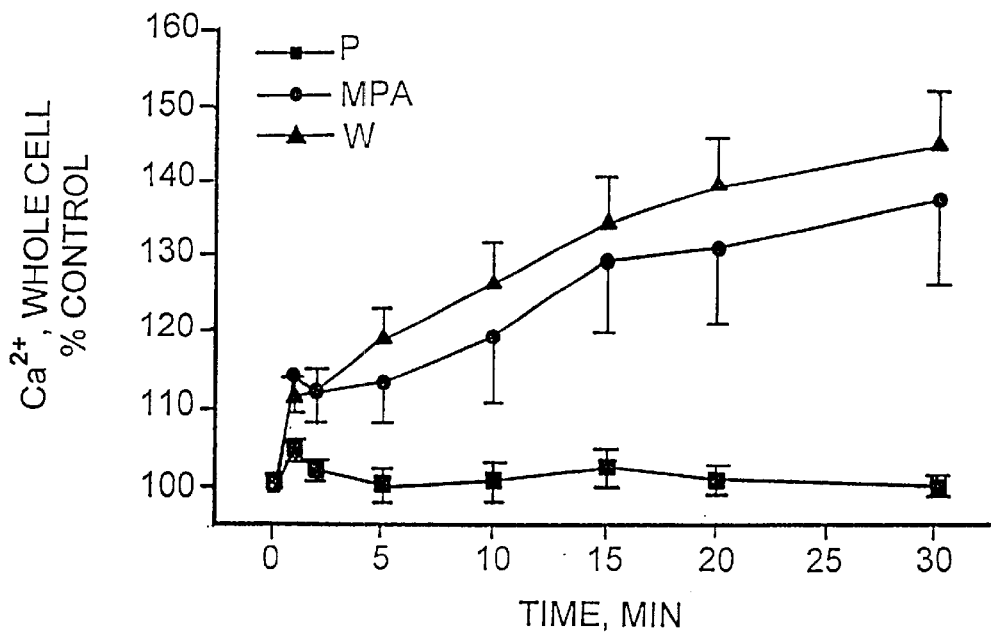
FIG. 3 is a graph depicting the changes in normalized calcium signals after stimulation by serotonin and U46619 in vascular muscle cells (VMC) in the withdrawal group (W), the progesterone group (P), or the medroxyprogesterone acetate group (MPA).
Figure 4:
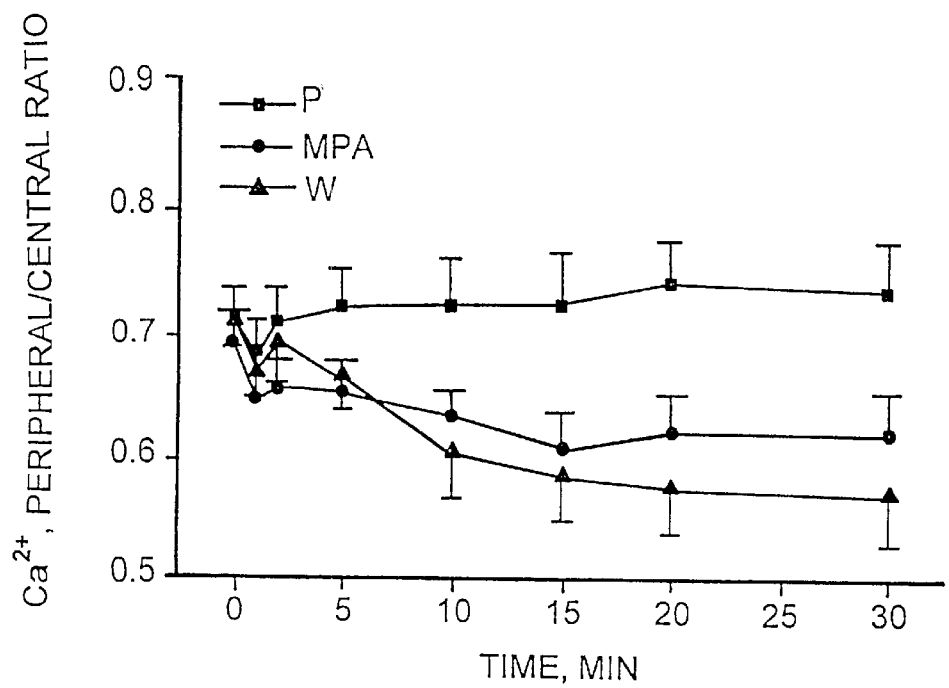
FIG. 4 is a graph depicting the changes in peripheral-to-central ratio of calcium after stimulation by serotonin and U46619 in VMC from W, MPA, or P-treated monkey coronary arteries.

Normalized (per pixel) changes in intracellular $Ca^{2+}$ levels are expressed as averages over whole VMC in FIG. 3 and as peripheral-to-central ratios in FIG. 4. After stimulation with 10 μM serotonin plus 100 nM U46619, VMC from E2-deprived (W) monkeys (triangles) showed an immediate increase in whole cell $Ca^{2+}$ fluorescence followed by a slow, sustained increase (significantly different from control value at 1 min and later; FIG. 3). FIG. 4 (triangles) shows that the peripheral-to-central ratio of $Ca^{2+}$ signal intensity decreased significantly at 5 min after stimulation and all later times in the W group. The ratio decreased because of $Ca^{2+}$ release from intracellular stores (e.g., SR).

MPA-treated monkey coronary artery VMC were strongly stimulated by 10 μM serotonin plus 100 nM U-146619, with progressively increasing $Ca^{2+}$. FIG. 3 (circles) plots averaged per pixel fluo 3 fluorescence intensity as a function of time. $Ca^{2+}$ was significantly increased over control averaged over the whole cell at 1 min and every subsequent time point. The immediate increase in $Ca^{2+}$ resulted from accelerated central $Ca^{2+}$ release, as indicated by the significantly decreased peripheral-to-central $Ca^{2+}$ ratio at 10 min and all subsequent times (FIG. 4, circles).

In contrast, coronary artery VMC from P-treated monkeys were only transiently stimulated by 10 μM serotonin plus 100 nM U46619. FIG. 3 (squares) plots per pixel averages of fluo 3 fluorescence showing that $Ca^{2+}$ increased significantly over control only at 1 min, and with a smaller peak than in W and MPA groups. The decrease in peripheral-to-central $Ca^{2+}$ localization ratio was too small to be significant and was already reversed at 2 min (FIG. 4, squares).

Averaged PKC Signals.

Figure 5:
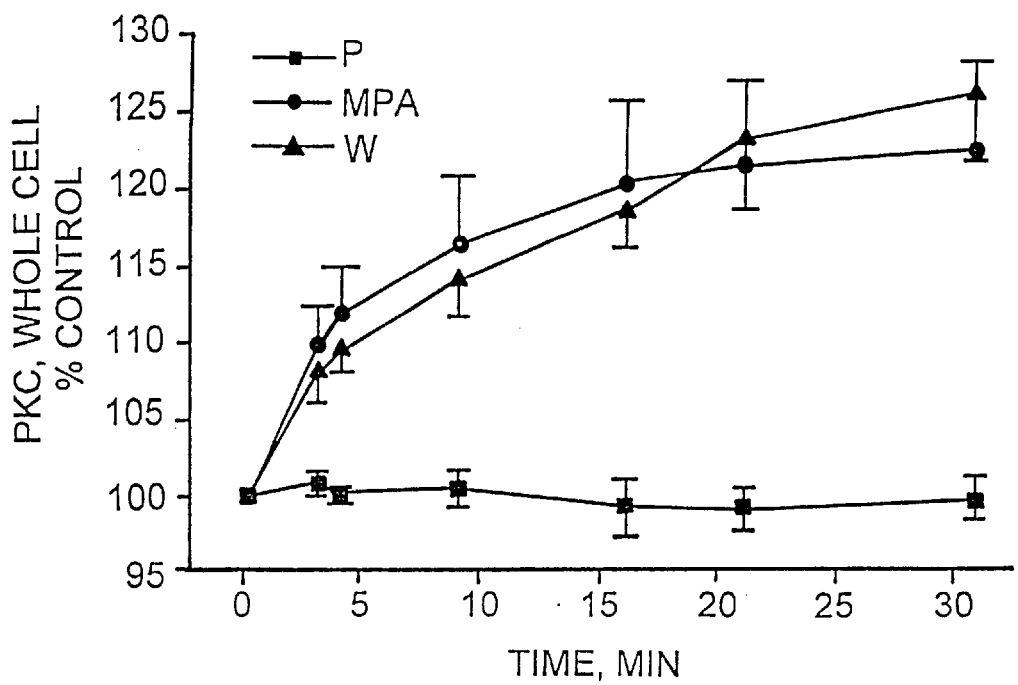
FIG. 5 is a graph depicting the changes in normalized protein kinase C (PKC) signals after stimulation in VMC from W, MPA, or P-treated monkey coronary arteries.
Figure 6:
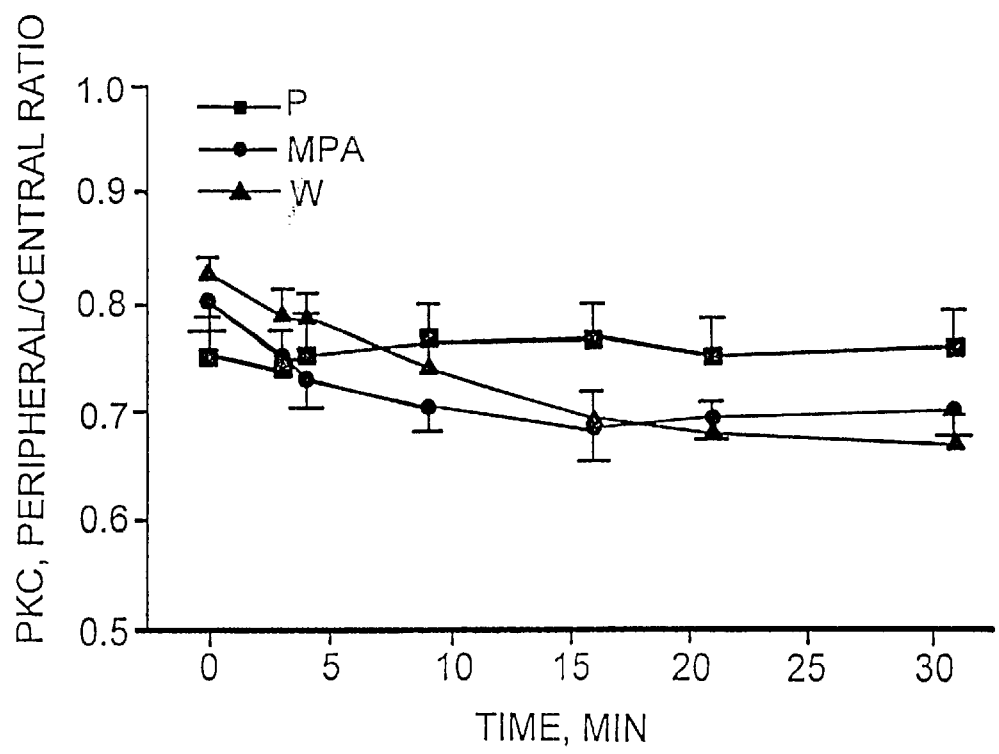
FIG. 6 is a graph depicting changes in peripheral-to-central PKC ratios after stimulation and VMC from W, MPA or P-treated monkey coronary arteries.

Normalized changes in PKC signal intensity are shown in FIGS. 5 and 6. Whole cell PKC signals of VMC in the W group (FIG. 4, triangles) increased at central and peripheral loci after stimulation with 10 $\mu$M serotonin plus 100 nM U46619, and continued to increase (significantly different from o-min control at 4 min and later). Peripheral-to-central PKC ratio decreased continuously and was significantly different from control at 16 min and subsequent times (FIG. 6, triangles).

In MPA, VMC, stimulation with 10 $\mu$M serotonin plus 100 nM U46619 caused PKC to increase at central and peripheral loci significantly above the 0-min control at 3 min and all subsequent time points. (FIG. 5, circles). Peripheral-to-central PKC ratio decreased significantly after stimulation with serotonin plus U46619 compared with control level at 9 min and all subsequent times (FIG. 6, circles).

In P VMC, stimulation with 10 $\mu$M serotonin plus 100 nM U46619 failed to change PKC loci or intensity significantly from control values (FIG. 5, squares), and peripheral-to-central PKC ratio was never significantly different from control (FIG. 6, squares).

Averaged Contractions.

Figure 7:
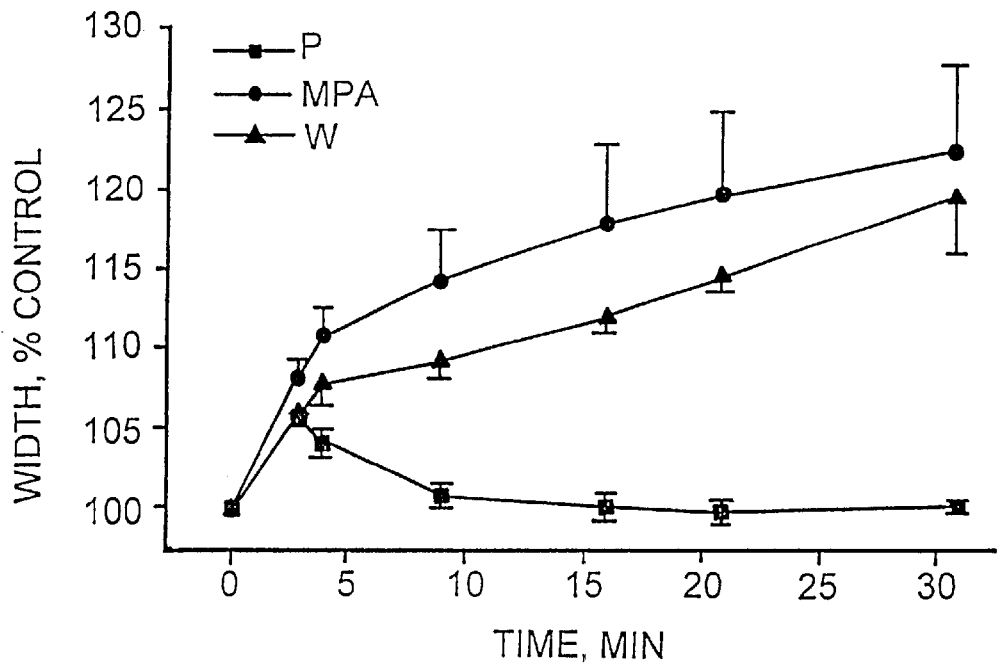
FIG. 7 is a graph depicting the change in the width of a VMC (indicating contractile element shortening) after stimulation from W, MPA or P-treated monkey coronary arteries.

Normalized changes in cell widths from primary cultured VMC are shown in FIG. 7. The width of VMC in all three groups increased significantly at 3 min after stimulation with 10 $\mu$M serotonin plus 100 nM U-46619, demonstrating VMC contractions but of different magnitude. Contractions indicated by central cell widening were significantly different from 0-min controls in W monkey VMC at 3 min and all subsequent times (FIG. 7, triangles). MPA group VMC contractions were significantly different from 0-min controls at 3 min and all subsequent times (FIG. 7, circles). P group VMC contractions were significantly different from 0-min controls only at 3 and 4 min (FIG. 7, squares).

Differences Among W. MPA. and P Groups.

Differences in W compared with P and MPA compared with P groups were found in all three parameters ($Ca^{2+}$, PKC, and contraction signals). Whole cell $Ca^{2+}$ fluorescence was greater in comparisons of both W and MPA groups with the P groups at 1 min after stimulation and all subsequent times (FIG. 3), and the peripheral-to-central ratio was less in W and MPA than P group VMC at 5 min and all subsequent times (FIG. 4). PKC signals were greater after stimulation in each of the W and MPA groups compared with the P group VMC at 4 min and all subsequent times (FIG. 5), but there was no significant difference in peripheral-to-central PKC ratios (FIG. 6). Contraction was significantly greater after stimulation in W and MPA than P group VMC at 4 min and all subsequent times (FIG. 7).

Based on comparisons of contractions, duration of activation by serotonin and U-46619 was between 4 and 9 min in P vs. >30 min in MPA and W groups. Contractions and increased $Ca^{2+}$ and PKC continued beyond 30 min, which we chose as the limit of the protocol.

EXAMPLE 4

An open label, controlled study was carried out in six healthy menopausal or post-menopausal women using no over-the-counter or prescription medications, medical foods or dietary supplements which would influence progesterone levels. Menopausal or post-menopausal status was determined by clinical methods. The inclusion criteria were low estrogen levels (less than or equal to 25 picograms per ml); non-use of progesterone for two weeks prior to the beginning of the study, and four weeks if medroxyprogesterone acetate was used; a body mass index less than 30; age between 40 and 65; non-smoker; at least six months after menopause (last bleeding); normal mammogram and pap smear within the past year; and reasonable reliability and client compliance. The exclusion criteria were: the history of cancer; history of thromboembolic disease; history of alcoholism in previous three years; current vaginal bleeding; mammogram suggesting malignant disease; history of diabetes melitis (defined as fasting blood sugar >1.4 mg/ml; history of renal disease defined as BUN >0.3 mg/ml or serum creatinine >0.02 mg/ml; current gall bladder disease; participation in any clinical trial involving either a marketed or investigational drug within 4 weeks; individual in which estrogen and progesterone therapy would be contraindicated; smoker. ProGest® cream was provided to each subject in a unit dose topical syringe containing 2 ml of cream. All other ingredients are inactive pharmaceutical necessities. The cream was to be applied in 2 ml amounts on calendar days 2–15 at 8 a.m. Applications were increased to a second 2 ml application at 8 p.m. on calendar days 16–30. In addition, estrogen was applied as a 7 day patch. The patch used was Vivelle®, Ciba (now Novartis), Summit N.J. The Vivelle® patch (0.05 mg/day) was applied on calendar days 0, 3, 7, 10, 14, 17, 21, 24 and 28.

Estrogen and progesterone serum levels were determined by chemiluminescence and were conducted on calendar days 2, 9, 16, 23, and 30 at times indicated.

| Week 0-Progesterone Levels: Nanograms/ml | | | | | | | |
|---|---|---|---|---|---|---|---|
| | ½ H | 1 H | 2 H | 3 H | 4 H | 6 H | 12 H |
| Patient 1 | 0.69 | 0.59 | 0.71 | 2.1 | 0.46 | 0.61 | 0.8 |
| Patient 2 | 0.47 | 0.52 | 0.68 | 0.84 | 0.75 | 2.9 | 1.7 |
| Patient 3 | 0.41 | 0.53 | 0.61 | 0.57 | 0.92 | 1 | 1.3 |
| Patient 4 | 1.1 | 1 | 1.3 | 1.3 | 1.2 | 1.3 | 2.2 |
| Patient 5 | 1.5 | 1.4 | 3. | 5.6 | 3.8 | 1.8 | 2.4 |
| Patient 6 | 1.6 | 3.1 | 2.8 | 3.5 | 3.3 | 4.6 | 2.4 |

| Week 1-Progesterone Levels: Nanograms/ml | | | | | | | |
|---|---|---|---|---|---|---|---|
| | 0 H | 1/2 H | 1 H | 2 H | 3 H | 4 H | 6 H | 12 H |
| Patient 1 | 0.43 | 1.0 | 0.84 | 0.49 | 1.0 | 0.96 | 0.98 | 0.87 |
| Patient 2 | 1.4 | 1.0 | 1.0 | 0.82 | 0.91 | 1.0 | 1.3 | 0.96 |
| Patient 3 | 1.3 | 1.5 | 1.4 | 1.0 | 0.94 | 1.1 | 2.0 | 1.3 |
| Patient 4 | 1.5 | 1.3 | 1.1 | 1.2 | 1.2 | 1.1 | 1.3 | 1.6 |
| Patient 5 | 1.6 | 1.6 | 1.3 | 1.1 | 1.7 | 1.3 | 1.6 | 1.8 |
| Patient 6 | 1.9 | 2.0 | 2.7 | 1.4 | 1.6 | 2.3 | 1.6 | 2.0 |

| Week 2-Progesterone Levels: Nanograms/ml | | | | | | | |
|---|---|---|---|---|---|---|---|
| | 0 H | 1 H | 2 H | 4 H | 6 H | 8 H | 12 H | 24 H |
| Patient 1 | 0.93 | 0.82 | 1 | 1.1 | 1 | 0.94 | 0.84 | 0.81 |
| Patient 2 | 1.2 | 0.94 | 0.81 | 1.5 | 1.3 | 0.83 | — | 2 |
| Patient 3 | 0.96 | 1.2 | 1.2 | 1.2 | 1.2 | 1.2 | 0.94 | 1.1 |
| Patient 4 | 2 | 1.3 | 1.7 | 2.4 | 1.5 | 1.1 | 1.2 | 0.98 |
| Patient 5 | 1.7 | 14.1 | 3.3 | 5 | 3.2 | 3 | 2.8 | 2.1 |
| Patient 6 | 3.3 | 2.4 | 2.9 | 1.8 | 2.9 | 2.2 | 3.1 | 1.5 |

Week 3-Progesterone Levels: Nanograms/ml

|  | 0 H | 1 H | 2 H | 4 H | 6 H | 8 H | 12 H | 24 H |
|---|---|---|---|---|---|---|---|---|
| Patient 1 | 0.91 | 0.79 | 0.74 | 1.5 | 0.95 | 0.73 | 0.63 | 0.47 |
| Patient 2 | 1.5 | 0.78 | 2.1 | 5.6 | 3.7 | 4.1 | 1.2 | 1.3 |
| Patient 3 | 1.7 | 1.2 | 2 | 1.4 | 1.1 | 1.1 | 1.5 | 1 |
| Patient 4 | 2.2 | 2.1 | 1.6 | 1.6 | 2.4 | 1.7 | 2.1 | 1.7 |
| Patient 5 | 2.6 | 6.9 | 2 | 1.6 | 3 | 3.8 | 1.8 | 4.4 |
| Patient 6 | 2.4 | 1.6 | 7.1 | 6.1 | 3.8 | 2.1 | 2.7 | 4.5 |

Week 4-Progesterone Levels: Nanograms/ml

|  | 0 H | 1 H | 2 H | 4 H | 6 H | 8 H | 12 H | 24 H |
|---|---|---|---|---|---|---|---|---|
| Patient 1 | 0.78 | 4.6 | 1.2 | 0.97 | 1.1 | 1.5 | 1.3 | 1.6 |
| Patient 2 | 2 | 1.3 | 2.7 | 4.5 | 2.7 | 1.3 | 3.4 | 2.4 |
| Patient 3 | 2.2 | 1.5 | 2.2 | 3 | 1.5 | 1.1 | 1.7 | 1.4 |
| Patient 4 | 2.1 | 1.5 | 1.5 | 1.8 | 2.7 | 2.7 | 2.1 | 2 |
| Patient 5 | 2.1 | 3.5 | 2 | 4 | 2.4 | 3.8 | 2.8 | 5.9 |
| Patient 6 | 1.9 | 2.8 | 4.2 | 3.1 | — | 3.7 | 2.1 | 2.3 |

It was noted that on week two of treatment, Patient 5, the measurement at 1 hour was 14.1 nanograms/ml. This outline is believed to have arisen as a result of collecting the blood sample at a location close to where the progesterone was applied. Thus, the measurement was of a local concentration and not a systemic blood level concentration and was considered inaccurate.

We claim:

1. A method for prophylactically treating myocardial ischemia comprising administering to a subject in need thereof an effective amount of progesterone.

2. The method of claim 1 wherein the myocardial ischemia is acute myocardial ischemia and the subject is additionally administered an estrogen.

3. The method of claim 1 wherein the progesterone prophylactically treats myocardial ischemia by prophylactically treating coronary vasospasm.

4. A method for increasing the beneficial effects of estrogen for prophylactically treating acute myocardial ischemia, comprising administering to a subject being administered estrogen an effective amount of progesterone.

5. A method for prophylactically treating angina pectoris comprising administering to a patient in need thereof an effective amount of progesterone.

6. The method of claim 5 wherein the progesterone prophylactically treats angina pectoris by prophylactically treating coronary vasospasm.

* * * * *